United States Patent [19]
Siegle et al.

[11] 4,103,024
[45] Jul. 25, 1978

[54] NEMATICIDALLY AND ARTHROPODICALLY ACTIVE N-METHYL-N-(2-TOLUENESULPHONIC ACID METHYLAMIDE-N'-SULPHENYL)-2,2-DIMETHYL-2,3-DIHYDROBENZOFURA-NYL-(7)-CARBAMATE

[75] Inventors: Peter Siegle, Cologne; Engelbert Kühle, Berg.-Gladbach; Alfons Hartmann, Beckingen; Bernhard Homeyer, Leverkusen; Ingeborg Hammann, Cologne, all of Germany

[73] Assignee: Bayer Aktiengesellschaft, Leverkusen, Germany

[21] Appl. No.: 773,108

[22] Filed: Feb. 28, 1977

[30] Foreign Application Priority Data

Mar. 10, 1976 [DE] Fed. Rep. of Germany ....... 2609830

[51] Int. Cl.$^2$ ............................................. A01N 9/28
[52] U.S. Cl. ................................. 424/285; 260/346.73; 260/544 C
[58] Field of Search ................... 260/346.2 R, 346.73

[56] References Cited
U.S. PATENT DOCUMENTS 3,980,673  9/1976  Siegle et al. ................... 260/346.2 R Primary Examiner—Henry R. Jiles
Assistant Examiner—Bernard Dentz
Attorney, Agent, or Firm—Burgess, Dinklage & Sprung

[57] ABSTRACT

Nematicidally and arthropodicidally active N-methyl-N-(2-toluenesulphonic acid methylamide-N'-sulphenyl)-2,2-dimethyl-2,3-dihydrobenzofuranyl-(7)-carbamate of the formula

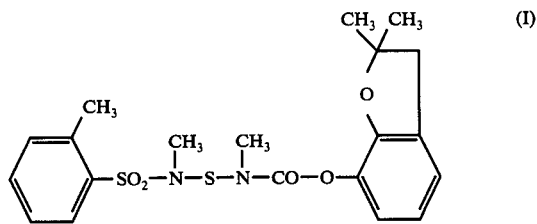

which possesses nematicidal and arthropodicidal properties.

3 Claims, No Drawings

NEMATICIDALLY AND ARTHROPODICALLY ACTIVE N-METHYL-N-(2-TOLUENESULPHONIC ACID METHYLAMIDE-N'-SULPHENYL)-2,2-DIMETHYL-2,3-DIHYDROBENZOFURANYL-(7)-CARBAMATE

The present invention relates to and has for its objects the provision of nematicidally and arthropodicidally active N-methyl-N-(2-toluenesulphonic acid methylamide-N'-sulphenyl)-2,2-dimethyl-2,3-dihydrobenzofuranyl-(7)-carbamate which possesses nematicidal and arthropodicidal properties, active compositions in the form of mixtures of such compound with solid and liquid dispersible carrier vehicles, and methods for producing such compound and for using such compound in a new way especially for combating pests, e.g. nematodes and arthropods, with other and further objects becoming apparent from a study of the within specification and accompanying examples.

It has been dislosed in U.S. Pat. No. 3,980,673 that certain N-methyl-N-(arylsulphonic acid methylamide-N'-sulphenyl)-2,2-dimethyl-2,3-dihydrobenzofuranyl-(7)-carbamates can be used as insecticides. The action of these compounds is generally good but is not completely satisfactory against some pests when the compounds are used at low concentrations.

The present invention now provides, as a new compound, N-methyl-N-(2-toluenesulphonic acid methylamide-N'-sulphenyl)-2,2-dimethyl-2,3-dihydrobenzofuranyl-(7)-carbamate, which has the formula

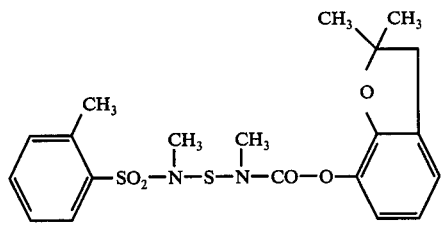

Surprisingly, the specific compound according to the invention, of the formula (I), exhibits a very powerful insecticidal action and surpasses the compounds of the same category known from U.S. Pat. No. 3,980,673; accordingly, the compound represents an enrichment of the art.

The present invention also provides a process for the preparation of the compound of the formula (I) in which (a) N-methyl-N-(2-toluenesulphonic acid methylamide-N'-sulphenyl)-carbamic acid fluoride, which has the formula

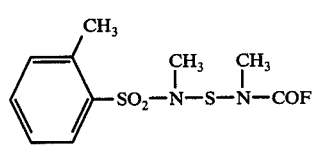

is reacted with 2,2-dimethyl-2,3-dihydrobenzofuranol-(7), which has the formula

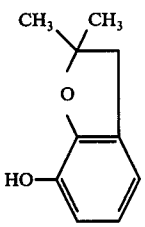

if appropriate in the presence of an acid-binding agent and of a diluent, or (b) 2,2-dimethyl-2,3-dihydrobenzofuranyl-(7)-N-methyl-carbamate, which has the formula

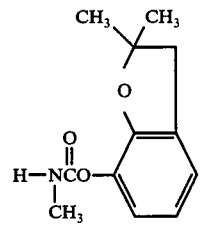

is reacted with the sulphenyl chloride of the formula

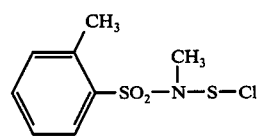

if appropriate in the presence of an acid-binding agent and of a diluent.

The course of the reaction, starting from the abovementioned compounds (II) and (III), can be represented by the following equation:

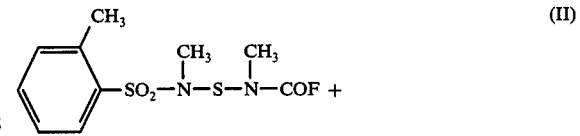

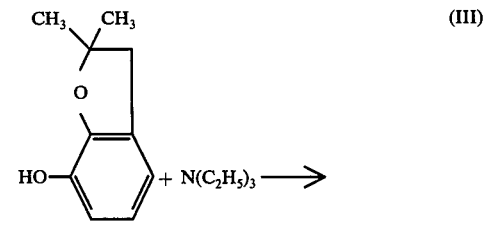

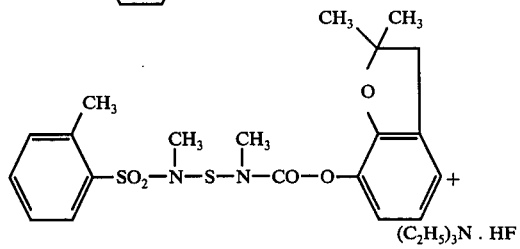

The acid fluoride of the formula (II) used as the starting material has not previously been described in the literature but can be prepared analogously to the process described in U.S. Pat. No. 3,954,836. For this, the starting material is 2-toluenesulphonic acid chloride, which is converted by means of methylamine to the corresponding sulphonic acid methylamide which is then converted to the disulphide by means of disulphur dichloride. Decomposition of this disulphide with chlorine gives the sulphenyl chloride (V), which can be reacted with N-methylcarbamic acid fluoride to give the compound of the formula (II).

2,2-Dimethyl-2,3-dihydrobenzofuranol-(7), also used as a starting material, is known.

Suitable diluents are all inert organic solvents. These include ethers such as diethyl ether, dioxane or tetrahydrofuran; hydrocarbons such as benzene or toluene; chlorohydrocarbons such as methylene chloride, chloroform or chlorobenzene; nitriles; esters; ketones; and mixtures of these solvents.

In order to bind the hydrogen halide formed during the reaction, a tertiary organic base, such as, for example, triethylamine or dimethylbenzylamine, is preferably added to the reaction mixture.

The reaction temperatures can be varied within a fairly wide range. In general, the reaction is carried out between 0° and 100° C, preferably at from 20° to 60° C.

Usually, the reactants are employed in equimolar amounts, but the use of an excess of one or other component is also possible.

As already mentioned, the active compound according to the invention is distinguished by a very good insecticidal activity, especially a soil-insecticidal activity. In addition, its activity against pests of stored products and pests harmful to health should also be mentioned.

The active compound is well tolerated by plants, has a favorable level of toxicity to warm-blooded animals, and can be used for combating arthropod pests, especially insects, and nematodes which are encountered in agriculture, in forestry, in the protection of stored products and of materials, and in the field. It is active against normally sensitive and resistant species and against all or some stages of development. The abovementioned pests include:

From the class of the *Isopoda*, for example *Oniscus asellus, Armadillidium vulgare* and *Porcellio scaber;* from the class of the *Diplopoda*, for example *Blaniulus guttulatus;* from the class of the *Chilopoda*, for example *Geophilus carpophagus l* and *Scutigera* spec.; from the class of the *Symphyla*, for example *Scutigerella immaculata;* from the order of the *Thysanura*, for example *Lepisma saccharina;* from the order of the *Collembola*, for example *Onychiurus armatus;* from the order of the *Orthoptera*, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the *Dermaptera*, for example *Forficula auricularia;* from the order of the *Isoptera*, for example *Reticulitermes* spp.; from the order of the *Anoplura*, for example *Phylloxera vastatrix, Pemphigus* spp., *Pediculus humanus corporis, Haematopinus* spp. and *Linognathus* spp.; from the order of the *Mallophaga*, for example *Trichodectes* spp. and *Damalinea* spp.; from the order of the *Thysanoptera*, for example *Hercinothrips femoralis* and *Thrips tabaci;* from the order of the *Heteroptera*, for example *Eurygaster* spp., *Dysdercus intermedius, Piesma quadrata, Cimex lectularius, Rhodnius prolixus* and *Triatoma* spp.; from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Rhorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homoa magnanima* and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera*, for example *Diprion* spp., *Hoplocampa* spp., *Lasius* spp., *Monomorium pharaonis* and *Vespa* spp.; from the order of the *Diptera*, for example *Aëdes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.*

The plant-parasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp. and *Trichodorus* spp..

When used against hygiene pests and pests of stored products, the active compound is distinguished by an excellent residual activity on wood and clay as well as a good stability to alkali on limed substrates.

The active compound according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compounds, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compound with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier wehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl aryl-polyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compound may be employed alone or in the form of mixtures with such solid and/or liquid dispersible carrier vehicles and/or with other known compatible active agents, especially plant protection agents, such as other nematicides and arthropodicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95% , and preferably 0.01–95%, by weight of the mixture.

When used against nematodes, the preparations are generally applied to an area of agriculture in amounts of 1 to 100 kg of active compound per hectare, and are then incorporated into the soil.

The active compound can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. nematodes and arthropods, which comprises applying to at least one of correspondingly (a) such nematodes, (b) such arthropods, and (c) the corresponding habitat thereof, i.e. the locus to be protected, e.g. to a growing crop, to an area where a crop is to be grown or to a domestic animal, a correspondingly combative or toxic amount, i.e. nematicidally or arthropodicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compound of the present invention is illustrated, without limitation, by the following examples:

that all aphids had been killed; 0% meant that no aphids had been killed.

The active compounds, the concentrations of the active compound, the evaluation times and the results can be seen from the following table:

Table 1

Long-term action after watering/0.025% of active compound
(*Myzus persicae* on *Brassica oleracea*)

| Active compounds | | % destruction after a period of | | | | |
|---|---|---|---|---|---|---|
| | | 4 days | 8 days | 11 days | 15 days | 18 days |
| Cl—C₆H₄—SO₂—N(CH₃)—S—N(CH₃)—COO-[2,2-dimethylbenzofuran] (known) | (A) | 85 | 60 | 80 | 85 | 0 |
| CH₃—C₆H₄—SO₂—N(CH₃)—S—N(CH₃)—COO-[2,2-dimethylbenzofuran] (known) | (B) | 95 | 50 | 65 | 45 | 0 |
| 2-CH₃-C₆H₄—SO₂—N(CH₃)—S—N(CH₃)—COO-[2,2-dimethylbenzofuran] | (I) | 100 | 100 | 100 | 95 | 90 |

EXAMPLE 1

*Myzus* test (long-term action after watering)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were each watered with 50 ml of the preparation of the active compound in such a way that the said preparation penetrated into the soil without wetting the leaves of the cabbage plants. The active compound was taken up by the cabbage plants from the soil and thus passed to the leaves.

After the specified periods of time, the plants were infested with aphids (*Myzus persicae*). The destruction in % was determined at intervals of 3 days. 100% meant

EXAMPLE 2

*Euscelis* Test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) were sprayed with the preparation of the active compound until dew-moist and were then infested with cicadas (*Euscelis bilobatus*).

After the specified period of time, the degree of destruction was determined in %. 100% meant that all cicadas had been killed; 0% meant that none of the cicadas had been killed.

The active compounds, the concentrations of the active compounds, the evaluation times and results can be seen from the following table:

Table 2

(Insects which damage plants)
*Euscelis* test

| Active compounds | | Active compound concentration in % | Degree of destruction in % after 3 days |
|---|---|---|---|
| 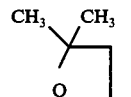 (known) | (A) | 0.1<br>0,02<br>0.004 | 100<br>75<br>20 |
| 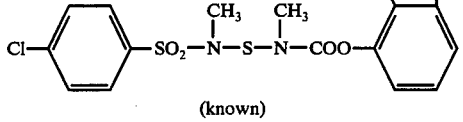 | (I) | 0.1<br>0.2<br>0.004 | 100<br>100<br>100 |

EXAMPLE 3

Root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given herein in ppm (= mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the abovementioned test insects after 7 days. After a further 2 days, the results were evaluated by counting or estimating the dead insects. The root-systemic action of the active compound was deduced from the destruction data. It was 100% when all test insects had been killed and 0% when just as many test insects were still alive as in the case of the untreated control.

The active compounds, the amounts used and the results can be seen from the following table:

Table 3

Root-systemic action
(*Myzus persicae*)

| Active compound | | Degree of destruction in % at an active compound concentration, of 10 ppm |
|---|---|---|
| 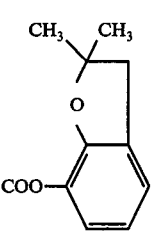 (known) | (B) | 0% |

Table 3-continued

Root-systemic action
(*Myzus persicae*)

| Active compound | | Degree of destruction in % at an active compound concentration, of 10 ppm |
|---|---|---|
| [Structure: 2-CH₃-phenyl-SO₂-N(CH₃)-S-N(CH₃)-COO-(2,2-dimethyl-benzofuran)] | (I) | 100% |

EXAMPLE 4

Root-systemic action
Test insect: *Phaedon cochleariae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given herein in ppm (= mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the abovementioned test insects after 7 days. After a further 2 days, the results were evaluated by counting or estimating the dead insects. The root-systemic action of the active compound was deduced from the destruction data. It was 100% when all test insects had been killed and 0% when just as many test insects were still alive as in the case of the untreated control.

The active compounds, the amounts used and the results can be seen from the following table:

Table 4

Root-systemic action
*Phaedon cochleariae* larvae

| Active compound | | Degree of destruction in % at an active compound concentration, of 10 ppm |
|---|---|---|
| [Structure: 4-CH₃-phenyl-SO₂-N(CH₃)-S-N(CH₃)-COO-(2,2-dimethyl-benzofuran)] (known) | (B) | 0% |
| [Structure: 2-CH₃-phenyl-SO₂-N(CH₃)-S-N(CH₃)-COO-(2,2-dimethyl-benzofuran)] | (I) | 100% |

EXAMPLE 5

Test nematode: *Meloidogyne incognita*
Solvent; 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given herein in ppm (= mg/l), was decisive. The soil was filled into pots, lettuce was sown in and the pots were kept at a greenhouse temperature of 27° C.

After 4 weeks, the lettuce roots were examined for infestation with nematodes (root knots), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from the following table:

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted herein in ppm (= mg/l). The soil was filled into pots and the pots were left to stand at room temperature.

After 24 hours the test insects were introduced into

Table 5

Nematicides
(*Meloidogyne incognita*)

| Active compound | | Degree of destruction in % at an active compound concentration of 10 ppm |
|---|---|---|
| CH₃-C₆H₄-SO₂-N(CH₃)-S-N(CH₃)-COO-C₆H₄-C(CH₃)₂-CH₂-O (benzofuran) (known) | (B) | 0% |
| 2-CH₃-C₆H₄-SO₂-N(CH₃)-S-N(CH₃)-COO-C₆H₄-C(CH₃)₂-CH₂-O (benzofuran) | (I) | 100% |

EXAMPLE 6

Soil insects
Test insect: *Phorbia antiqua* grubs in the soil
Solvent: 3 parts by weight of acetone
Emulsifier: 1 part by weight of alkylaryl polyglycol ether the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

Table 6

Soil insecticides
*Phorbia antiqua* grubs in the soil

| Active compound | | Degree of destruction in % at an active compound concentration, of 10 ppm |
|---|---|---|
| CH₃-C₆H₄-SO₂-N(CH₃)-S-N(CH₃)-COO-C₆H₄-C(CH₃)₂-CH₂-O (benzofuran) (known) | (B) | 0% |

Table 6-continued
Soil insecticides
*Phorbia antiqua* grubs in the soil

| Active compound | Degree of destruction in % at an active compound concentration, of 10 ppm |
|---|---|
| 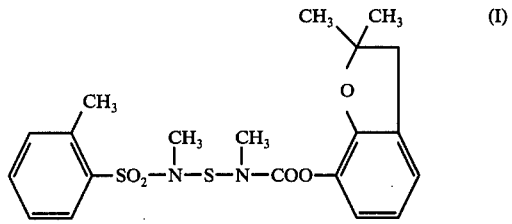 (I) | 100% |

The synthesis of the novel compound is shown in the following example:

EXAMPLE 7

(a) The acid fluoride required as the starting compound could be obtained as follows:

67.5 g (0.5 mol) of disulphur dichloride were added dropwise, at 25° C, to 185 g (1 mol) of 2-toluenesulphonic acid methylamide and 101 g (1 mol) of triethylamine in 2 liters of toluene, the mixture was stirred for a further 6 hours at room temperature and 1 hour at 40° C and was extracted by shaking twice with water and once with 10 per cent strength aqueous ammonium chloride solution, and the organic phase was evaporated in vacuo. The residue was taken up in chloroform. 78 g (1.1 mol) of chlorine gas were passed into this solution at 20° C. The mixture was left to stand overnight and then evaporated in vacuo.

The sulphenyl chloride thus obtained was dissolved, together with 77 g (1 mol) of N-methyl-carbamic acid fluoride, in 2 liters of toluene, and 101 g (1 mol) of triethylamine were added while stirring at 25° C. The mixture was stirred for a further 6 hours at 25° C and 1 hour at 40° C and was extracted by shaking twice with water and twice with 10 per cent strength aqueous ammonium chloride solution, and the organic phase was concentrated in vacuo, giving 258 g of N-methyl-N-(2-toluenesulphonic acid methylamide-N'-sulphenyl)carbamic acid fluoride; $n_D^{20}$: 1.5571.

b) (I)

10.1 g (0.1 mol) of triethylamine were added dropwise, while stirring at 25–30° C, to 29.2 g (0.1 mol) of N-methyl-N-(2-toluenesulphonic acid methylamide-N'-sulphenyl)-carbamic acid fluoride and 16.4 g (0.1 mol) of 2,2-dimethyl-2,3-dihydrobenzofuranol-(7) in 200 ml of absolute toluene. The mixture was stirred for a further 4 hours at room temperature and 1 hour at 50°–60° C and was extracted by shaking with ice-cold dilute sodium hydroxide solution, water and 10 per cent strength aqueous ammonium chloride solution, and the organic phase was dried over sodium sulphate. After evaporating the solvent in vacuo, 34.9g (80% of theory) of N-methyl-N-(2-toluenesulphonic acid methylamide-N'-sulphenyl)-2,2-dimethyl-2,3-dihydrobenzofuranyl-(7)-carbamate were obtained in the form of a brown oil; $n_D^{20}$: 1.5634.

It will be appreciated that the instant specification and examples are set forth by way of illustration and not limitation, and that various modifications and changes may be made without departing from the spirit and scope of the present invention.

What is claimed is:

1. N-Methyl-N-(2-toluenesulphonic acid methylamide-N'-sulphenyl)-2,2-dimethyl-2,3-dihydrobenzofuranyl-(7)-carbamate, of the formula

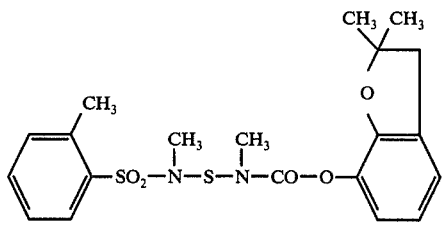

2. A nematicidal or arthropodicidal composition containing as active ingredient a nematicidally or arthropodicidally effective amount of the compound according to claim 1 in admixture with a diluent.

3. A method of combating nematodes or arthropods which comprises applying to the nematodes or arthropods, or to a habitat thereof a nematicidally or arthropodicidally effective amount of the compound according to claim 1.

* * * * *